United States Patent [19]

Feldman et al.

[11] Patent Number: 5,222,021
[45] Date of Patent: Jun. 22, 1993

[54] METHOD TO CORRECT THE MEASUREMENT OF THE BONE DENSITY IN A SCANNER USING A CALIBRATION PHANTOM HAVING TWO INSERTS

[75] Inventors: Andréi Feldman, Paris; Philippe Giudici, Garches, both of France

[73] Assignee: General Electric CGR S.A., Issy les Moulineaux, France

[21] Appl. No.: 552,134

[22] Filed: Jul. 13, 1990

[30] Foreign Application Priority Data

Jul. 20, 1989 [FR] France .................. 89 09781

[51] Int. Cl.⁵ .............................. G06F 15/42
[52] U.S. Cl. ..................... 364/413.14; 378/18; 364/413.15
[58] Field of Search ........... 364/413.14, 413.15, 364/413.17, 571.01, 571.02, 571.05, 581; 378/18, 48, 56, 207

[56] References Cited

U.S. PATENT DOCUMENTS

| | | | |
|---|---|---|---|
| 4,118,628 | 10/1978 | Hounsfield | 364/413.15 |
| 4,149,081 | 4/1979 | Seppi | 378/18 |
| 4,233,507 | 11/1980 | Volz . | |
| 4,352,020 | 9/1982 | Horiba et al. . | |
| 4,651,335 | 3/1987 | Kalender et al. | 378/207 |
| 4,782,502 | 11/1988 | Schulz | 378/207 |
| 4,809,172 | 2/1989 | Hopkinson et al. | 364/571.05 |
| 4,947,414 | 8/1990 | Stein | 378/56 |
| 4,985,906 | 1/1991 | Arnold | 378/18 |

FOREIGN PATENT DOCUMENTS 218367 4/1987 European Pat. Off. .

*Primary Examiner*—Robert A. Weinhardt
*Attorney, Agent, or Firm*—Nilles & Nilles

[57] ABSTRACT

The disclosure concerns X-ray scanners and, more particularly, a method to measure the bone density of a patient that takes his or her build into account. The disclosed method consists in performing a calibration of the bone density measurement by means of a phantom that simulates the patient's body and the vertebra an calibration phantom comprising a water insert and an insert with a high concentration of $K_2HPO_4$. A measurement is made of the densities of several inserts of different concentrations and of the concentration of the water insert and of the $K_2HPO_4$ high concentration insert, in the presence and without the presence of the bag of water, enabling the computation of corrections of the measured density of the patient's vertebra depending on his or her build.

10 Claims, 2 Drawing Sheets

METHOD TO CORRECT THE MEASUREMENT OF THE BONE DENSITY IN A SCANNER USING A CALIBRATION PHANTOM HAVING TWO INSERTS

BACKGROUND OF THE INVENTION

The invention concerns X-ray scanners and, more particularly in such scanners, a method for the measurement of the bone density of a patient, enabling the density measurement to be corrected as a function of the patient's build.

DESCRIPTION OF THE PRIOR ART

For examining patients, it is becoming increasingly common to use X-ray instruments called "scanners" which take cross-sectional images of the patient. These instruments are based on the physical phenomenon of absorption of X-rays by the human body. This absorption is directly related to the distance x travelled by the X-rays in the body according to the formula:

$$I = I_o e^{-bx}$$

where:
- $I_o$ is the intensity of the radiation entering the human body,
- I is the intensity of the radiation leaving the human body,
- b is a coefficient of attenuation depending on the body that the radiation goes through.

In a logarithmic scale of measurement, the attenuation $I/I_o$ is equal to bx, i.e. it is proportionate to the distance x.

As can be seen in FIG. 1, these instruments consist essentially of an X-ray source 10 associated with a detection device 11. These two elements are positioned with respect to one another in a fixed geometrical relationship so that a body 15 to be examined can be interposed between them. Furthermore, they are supported by a structure (not shown) which can rotate around the body to be examined so as to irradiate the body at different angles. The X-ray source, which is controlled by a device 13, emits its rays in an angular sector which has a width sufficient to illuminate the entire cross-section of the body 15. The detection device 11 has the shape of a sector of an annulus, the length of which is adapted to the width of the X-ray beam and consists of a large number of elementary detectors 12 juxtaposed with one another.

To obtain an image of the cross-section of the body 15 crossed by the X-ray beam, the support structure of the source 10 and of the detection device 11 is made to rotate around the body 15 and the output signals from the elementary detectors 12 are measured so as to be processed appropriately in an electronic device 14 according to prior art methods so as to draw a representative image of the cross-section therefrom.

Each elementary dot of the image representing the cross-section has a luminosity, the value of which indicates the absorption of X-radiation undergone by this corresponding part of the object. Hence, the idea came up of using an image such as this to measure the bone density of a patient's skeleton, generally by performing this measurement for the lumbar vertebrae.

To make a measurement of bone density, it is necessary first of all to do a calibration of the instrument by means of several inserts of a solution of di-potassium hydrogen phosphate ($K_2HPO_4$), the energy behavior of which is equivalent to that of the spongy part of a lumbar vertebra. In practice, a phantom 20 (FIG. 2) is used. This phantom 20 is placed beneath a patient 26 in the zone of a lumbar vertebra 28.

This phantom 20 has, for example, five cylindrical holes 21 to 25 into which cylindrical tubes 21' to 25' are introduced. One tube 21' contains water and the other four tubes 22' to 25' respectively contain a solution of $K_2HPO_4$ with a different concentration respectively, for example 50 mg/cc, 100 mg/cc, 150 mg/cc and 200 mg/cc. When the patient 26 is placed on a bed 27, an examination is made so as to obtain the image of a cross-section of the patient's body at the lumbar vertebrae. This image comprises the lumbar vertebra 28 and the tubes or inserts 21' to 25'. The image of the inserts is brighter with higher concentration levels of the $K_2HPO_4$ solution.

Since each elementary dot of the image, called a pixel, has a luminosity representing a density that is measured according to an appropriate scale, in Hounsfield levels or units HL, it is possible to plot the curve 30 of FIG. 3 connecting the dots 31 to 35, representing the density of the inserts 21' to 25' measured in Hounsfield levels NH. Thus, if the measurement for the vertebra 28 is NH1 on the y-axis, it will be deduced therefrom that its density is equivalent to that of a concentration C1 of $K_2HPO_4$: this corresponds to a determined bone density.

The method for describing the bone density of a vertebra, that has just been briefly described, lacks precision. One of the main sources of error is the fact that the patient's build plays a major role in the density of the objects.

This phenomenon is explained by the fact that X-ray beam used by the scanners is polychromatic, with a large percentage of photons located in a low-energy spectral zone. The method for reconstructing an image takes this fact into account and introduces a mathematical correction that compensates for the relatively higher attenuation of the low-energy photons. This compensation will be all the greater as the attenuation is high, and this is the case when the patient is heavily built for the filtering of the low-energy photons by the human body is all the greater as this body is bulky.

For a scanner in which the beam energy is homogeneous along the detection device, the corrected value X' of an attenuation X will be given by the formula:

$$X' = X + A_1 X^2 + A_2 X^3 + \ldots A_n X^{n+1}$$

The coefficients $A_1, A_2 \ldots A_n$ depend on a great many parameters such as the nature of the anode, of the object examined or of the detection device. These coefficients are computed for the case where the body of the patient examined contains above all tissues that essentially consist of water. The coefficients are thus optimized for a water phantom so that the density measured on the corrected image is homogeneous throughout its surface.

If, in the field of the X-ray beam, there should be a water phantom and an object with an atomic mass different from that of water, for example the calcium of a bone of the skeleton, the coefficients $A_1, A_2 \ldots A_n$ determined with a water phantom are no longer valid for a ray of the beam crossing, at the same time, the water phantom and the object.

In effect, the beam, received by the detection device and attenuated by the object made of calcium, will correspond to optical paths having different lengths in water. Now, the longer the path in the water, the greater will be the shift of the mean energy of the beam towards the high energy values. This corresponds to a hardening of the beam so that the beam will be less attenuated by the calcium object. The result thereof is that, for a heavily built patient, the measurement of the calcium density will be under-estimated as compared with that of a more slightly built patient.

The result thereof is that the calibration curve measured will be affected by this phenomenon and will give the points 32' to 35' corresponding to a mean curve 36, which gives lower densities than the mean values.

Thus, the current method leads to an error in measurement (C3−C2) arising, firstly, from the fact that the measured value NH2 corresponds to a concentration C2 on the measured curve 36 and, secondly, from the fact that this value NH2 is under-estimated and should be NH3 which would correspond to a concentration C3 on the theoretical curve 30.

SUMMARY OF THE INVENTION

The aim of the present invention, therefore, is to implement a method that enables the elimination of this error of measurement in the conventional method, in taking the patient's build into account.

The invention concerns a method for correcting the measurement of the bone density in an X-ray scanner, comprising the following operations:

(a) the positioning, in the field of the scanner, of a phantom simulating the body of a patient of slight build and comprising a cavity to receive an insert simulating a vertebra;

(b) the positioning, under the simulation phantom, of a calibration phantom comprising two cavities, of which the first is intended to receive an insert containing water and the second is intended to receive an insert containing a solution with a high concentration of di-potassium hydrogen phosphate ($K_2HPO_4$);

(c) the positioning in the cavity of the simulation phantom of an insert containing a solution of $K_2HPO_4$ with a concentration AO and the measurement of the following densities:

$V_c(1)$ of the solution contained in the insert simulating the vertebra;

$D_1(E)$ of the water contained in the first calibration insert, and $D_1(S)$ of the solution contained in the second calibration insert;

(d) the positioning of a bag of water on the simulation phantom and the measurement of the following densities:

$V_m(1)$ of the solution contained in the insert simulating the vertebra;

$D'_1(E)$ of the water contained in the calibration insert and, $D'_1(S)$ of the solution contained in the calibration insert;

(e) the computation of $$D_{HD}(1) = [D_1(S) - D_1(E)] - [D'_1(S) - D'_1(E)]$$

Which indicates the changing of the density of the solution contained in the second calibration insert due to the presence of the bag of water with respect to the density of the first insert;

f) the reiteration of the operations (c), (d) and (e) for n inserts simulating the vertebra containing solutions of concentrations Al to An different from AO, so as to obtain, for each new concentration, other values of $V_c$, $V_m$ and $D_{HD}$ (g) the computation of the correction coefficients $a_o$ to $a_n$ of the n degree polynomial such that:

$$V_c = V_m + \sum_{n=0}^{n} a_n V_c^n \cdot D_{HD}$$

It further comprises the following operations:

(h) the computation of the mean value of the differences in densities $[D_{(i)}(S) - D_i(E)]$ between the $K_2HPO_4$ solution and water for the n inserts (39) simulating the vertebra so as to obtain the difference:

$$D(S) - D(E) = \frac{\sum_{i=1}^{n} [D_i(S) - D_i(E)]}{n}$$

To do the correction during the measurement of the patient's bone density, the procedure should be complemented by the following operations:

(i) the positioning of the patient in the place of the simulation phantom and the measurement of the following densities:

$V_m(VER)$ of the patient's vertebra which is in coincidence with the calibration phantom, $D_m(E)$ of the water contained in the first calibration insert, $D_m(S)$ of the solution contained in the second insert, (j) the computation of the difference $$D_{HD} = [D(S) - D(E)] - [D_m(S) - D_m(E)]$$

(k) the computation of the corrected value $V_c(Ver) > V_m(Ver)$ of the bone density of the patient's vertebra (VER) which meets the equation:

$$V_c(Ver) = V_m(Ver) + \sum_{n=0}^{n} a_n V_c^n (Ver) \cdot D_{HD}$$

the coefficients $a_n$ being those obtained by the operation (g).

Preferably, the correction will be done according to a second degree polynomial so that the calibration is restricted to the positioning of the three different inserts simulating the vertebra.

BRIEF DESCRIPTION OF THE DRAWINGS

Other features and advantages of the present invention will appear from the following description of a particular exemplary embodiment, said description being made with reference to the appended drawings wherein.

DESCRIPTION OF PREFERRED EMBODIMENTS

The correction method according to the invention is based on the fact that, for a given scanner and for a given calibration phantom, the difference in density measured between the water insert and that of the high concentration would be a constant were the patient to have always the same build. When this difference changes, it can only be due to the patient's build. Since this build also affects the measured value $V_m$ of the density of the vertebra, the change in density $D_{HD}$ measured on the high concentration insert due to the build is exploited in order to correct the density measured on the vertebra and obtain the corrected value $V_c$.

If the values $V_c$, $V_m$ and $D_{HD}$ are expressed in Hounsfield levels NH, the proposed correction will therefore have the form:

$$V_c = V_m + K(V_c) \cdot D_{HD} \qquad (1)$$

Should $K(V_c)$ be a second degree polynomial, we can write:

$$V_c = V_m + (a + bV_c + eV_c^2)D_{HD} \qquad (2)$$

where $$eD_{HD} V_c^2 + (bD_{HD} - 1)V_c + aD_{HD} - V_m = 0 \qquad (3)$$

The value $V_c$, which will be the solution of the equation 3, should be positive and greater than $V_m$.

To determine the value of the coefficients a, b and e of the polynomial $K(V_c)$, the invention proposes to perform the operations that shall be described hereinafter.

Figure 1:
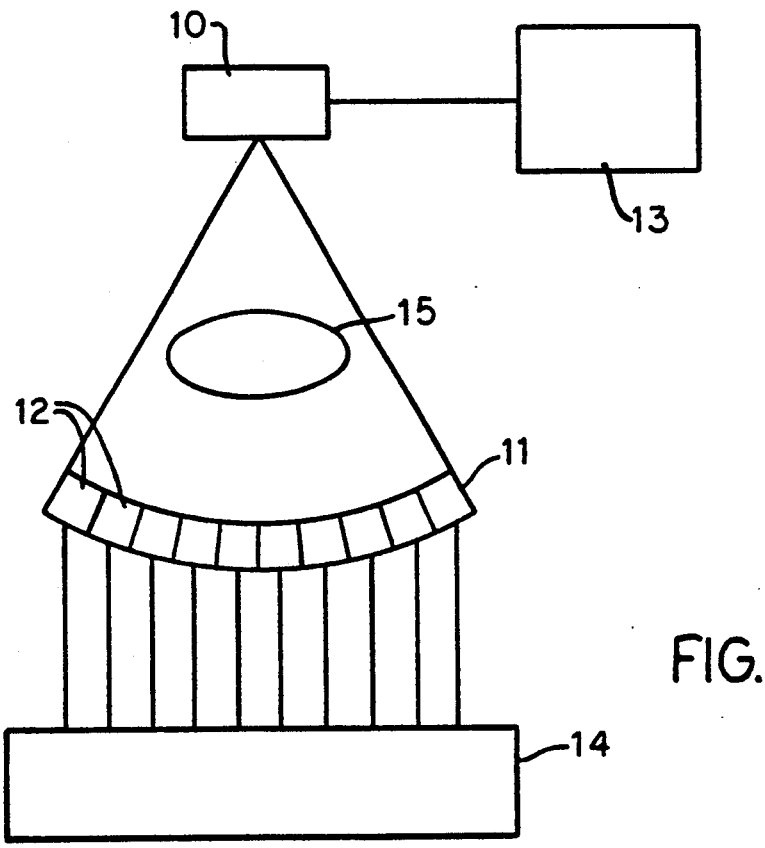
FIG. 1 is a schematic drawing of an X-ray scanner.
Figure 2:
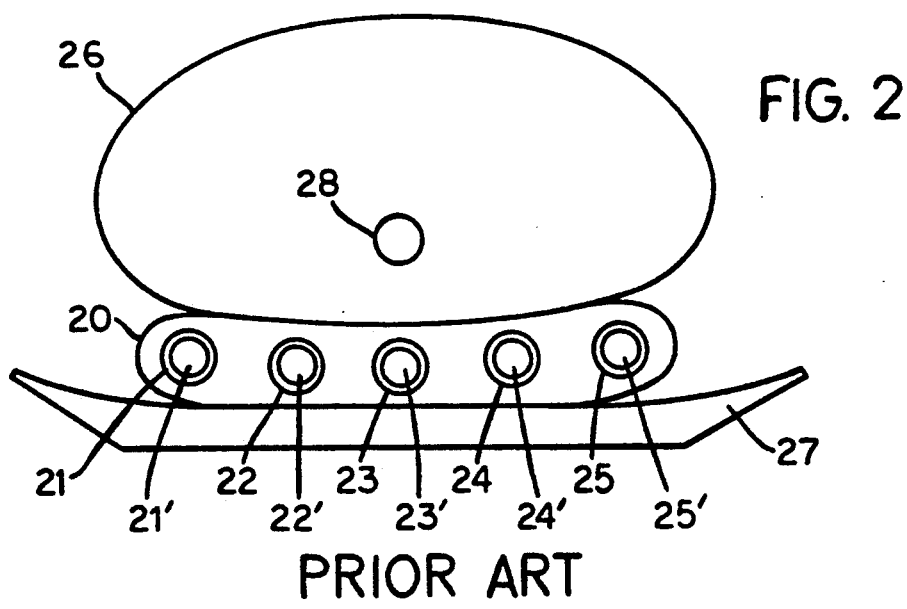
FIG. 2 shows the respective positions of the patient's body and of the phantom with calibration inserts used in the prior art methods.
Figure 3:
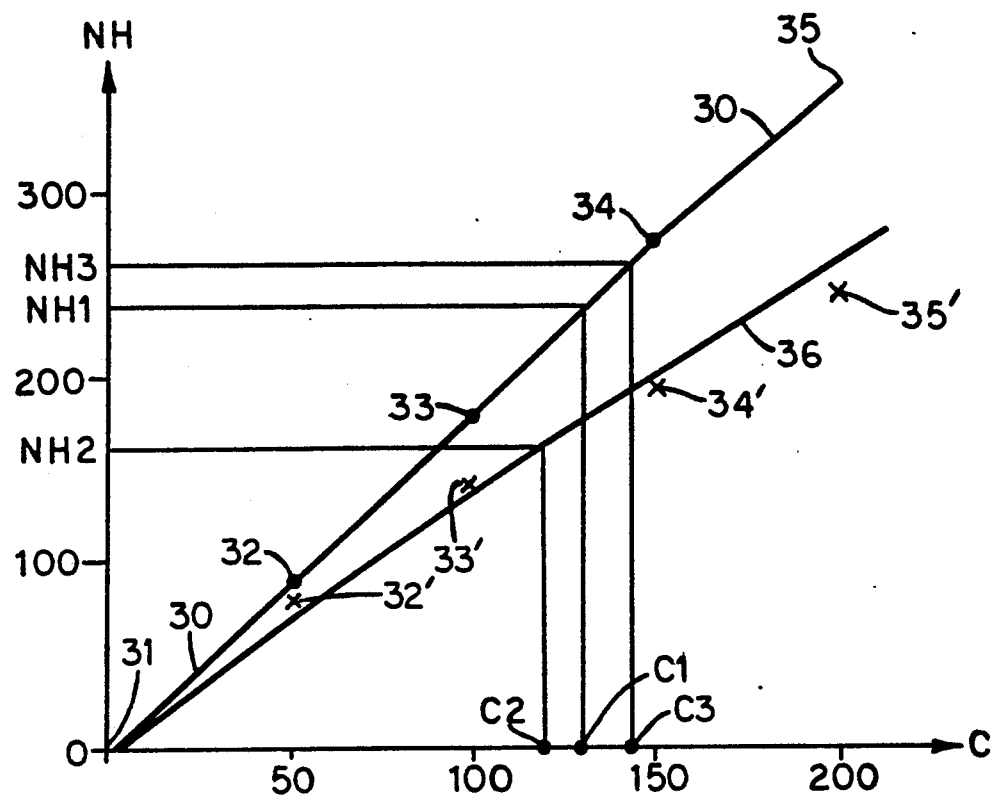
FIG. 3 uses curves to show the effect of the patient's build on the measurement of the bone density.
Figure 4:
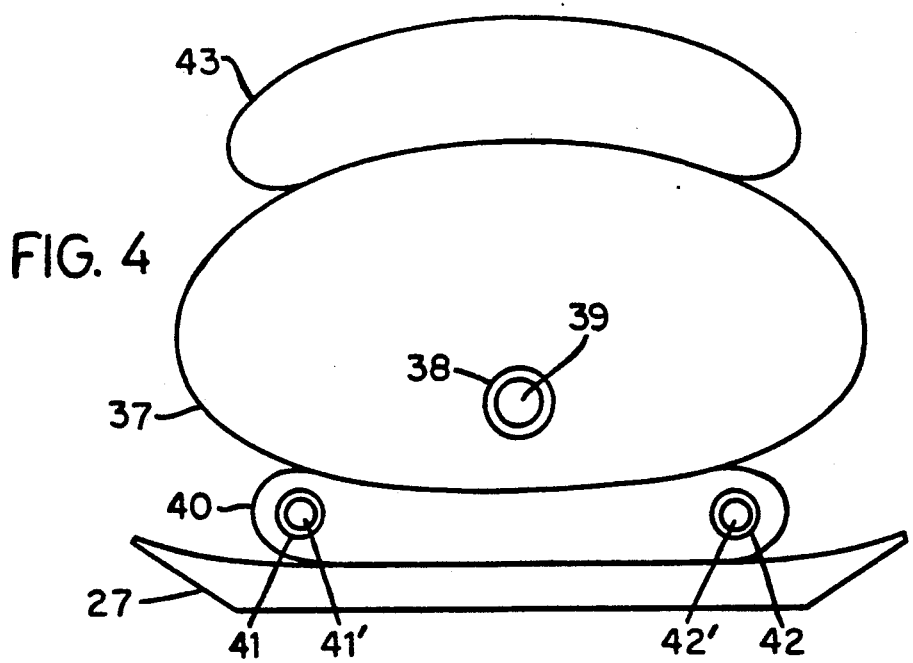
FIG. 4 shows the phantom of simulation of the patient's body and that of the calibration, which are used to implement the method according to the invention.

The first operation consists in placing a phantom 37 (FIG. 4) in the field of a scanner such as the scanner 10 in FIG. 1. This phantom 37 simulates the body of a patient of slight build, and has a cavity 38 to receive an insert 39 simulating a lumbar vertebra. Beneath this phantom 37 simulating the patient's body, a calibration phantom 40 is placed. This calibration phantom 40 has two cavities 41 and 42, one of which is capable of containing an insert 41' filled with water while the other is capable of containing a solution of di-potassium hydrogen phosphate ($K_2HPO_4$) in a high concentration, for example 250 mg/cc.

For a first series of measurements, an insert 39 containing a $K_2HPO_4$ solution, of low concentration, for example 50 mg/cc, is introduced into the insert 39 of the simulation phantom. On the image obtained after one exploratory revolution of the scanner, the following densities are measured:

$V_c(1)$ of the solution contained in the insert (39) simulating the lumbar vertebra, $D_1(E)$ of the water contained in the insert 41', $D_1(S)$ of the solution contained in the insert 42'.

Then a bag of water 43 is placed on the simulation phantom 37 to simulate a heavily built patient, doing so in combination with the phantom 37. After an exploratory revolution of the scanner, the following densities are measured:

$V_m(1)$ of the solution contained in the insert 39, $D'_1(E)$ of the water contained in the insert 41', $D'_1(S)$ of the solution contained in the insert 42'.

The computation $[D_1(S) - D_1(E)] - [D'_1(S) - D'_1(E)]$ will give the first value $D_{HD}(1)$ of $D_{HD}$.

This first series of measurements is repeated for an insert 39 with a mean concentration, for example 125 mg/cc, so as to obtain values $V_c(2)$, $V_m(2)$ and $D_{HD}(2)$, then for a high concentration insert, for example 200 mg/cc so as to obtain values $V_c(3)$, $V_m(3)$ and $D_{HD}(3)$.

The different values of $V_m$, $V_c$ and $D_{HD}$ which were obtained by the above-described operations enable the computation of the coefficients a, b and e of the polynomial $K(V_c)$ and, hence, the definition of the equation (2) to perform the corrections when bone density measurements are made on the patients.

The method for computing the coefficients a, b and e has been explained for the case where $K(V_c)$ is a 2-degree polynome. However, $K(V_c)$ may be an n-degree polynomial where n is greater than two and the different operations of the method for computing the (n+1) coefficients $a_0$ to $a_n$ of the polynomial are then the following:

(a) the positioning, in the field of the scanner, of a phantom (37) simulating the body of a patient of slight build and comprising a cavity (38) to receive an insert (39) simulating a vertebra;

b) the positioning, under the simulation phantom, of a calibration phantom (40) comprising two cavities (41, 42), of which the first is intended to receive an insert (41') containing water and the second is intended to receive an insert (42') containing a solution with a high concentration of di-potassium hydrogen phosphate ($K_2HPO_4$);

(c) the positioning in the cavity (38) of an insert (39) containing a solution of $K_2HPO_4$ with a concentration AO and the measurement of the following densities:

$V_c(1)$ of the solution contained in the insert (39) simulating the vertebra;

$D_1(E)$ of the water contained in the first calibration insert (41'), and $D_1(S)$ of the solution contained in the second calibration insert (42');

(d) the positioning of a bag of water (43) on the simulation phantom (37) and the measurement of the following densities:

$V_m(1)$ of the solution contained in the insert (39) simulating the vertebra;

$D'_1(E)$ of the water contained in the calibration insert (41'), and $D'_1(S)$ of the solution contained in the calibration insert (42'); (e) the computation of $$D_{HD}(1) = [D_1(S) - D_1(E)] - [D'_1(S) - D'_1(E)]$$

which indicates the changing of the density of the solution contained in the second calibration insert (42') due to the presence of the bag of water (43) with respect to the first calibration insert (41').

(f) the reiteration of the operations (c), (d) and (e) for n inserts simulating the vertebra containing solutions of concentrations A1 to $A_n$ different from AO, so as to obtain, for each new concentration, other values of $V_c$, $V_m$ and $D_{HD}$ (g) the computation of the correction coefficients $a_0$ to $a_n$ of the n-degree polynomial such that:

$$V_c = V_m + \sum_{n=0}^{n} a_n V_c^n \cdot D_{HD}$$

During the bone density measurements conducted on the patients, the calibration phantom has to be placed beneath the patient, and a measurement has to be made, firstly, of the density $V_m$ of the vertebra and, secondly, of the change in density $D_{HD}$ measured on the insert 42' of high concentration as compared with the water. The coefficients a, b and e being known by the above-described method, and knowing $V_m$ and $D_{DH}$ resulting from the measurement on the patient, the equation (3) enables the computation of $V_c$.

To measure the change in density $D_{HD}$ measured on the insert 42' of high concentration as compared with water, it is necessary to compute the difference:

$$[D(S) - D(E)] - [D_m(S) - D_m(E)]$$

that is, the difference between two terms, of which the first $[D(S) - D(E)]$ is the difference in densities between the $K_2HPO_4$ solution and the water of the calibration phantom when there is no water bag in the case of the measurements with the simulation phantom of the patient's body while the second term $[D_m(S) - D_m(E)]$ is the difference in densities between the $K_2HPO_4$ and the water in a case where the patient's body replaces the simulation phantom, with the calibration phantom staying in place.

It must be noted that the elements of the first term $[D(S) - D(E)]$ are measured during the calibration operations for each of the n inserts (39) for simulating the vertebra when there is no water bag, and the values thus measured are affected by the different concentrations of the solutions contained in the insert (39) simulating the vertebra. This effect is, however, very small as compared with the effect of the patient's build, and the invention proposes, in an operation designated as (h), to compute the mean value of this first term, namely the mean value of the differences $D_1(S) - D_1(E)$, $D_2(S) - D_2(E)$, ... $D_n(S) - D_n(E)$ which is expressed by:

$$\frac{\sum_{i=1}^{n}[D_i(S) - D_i(E)]}{n} = D(S) - D(E)$$

Instead of computing the mean value, it is possible to take only one of the differences $D_i(S) - D_{(i)}(E)$ among n, for example the one obtained with the insert corresponding to the most common bone density value.

During the measurement of the patient's bone density, the complementary operations to be performed to obtain a corrected value of the patient's bone density are then the following ones:

(i) the positioning of the patient in the place of the simulation phantom and the measurement of the following densities:

$V_m(Ver)$ of the patient's vertebra which is in coincidence with the calibration phantom (40), $D_m(E)$ of the water contained in the first calibration insert (41'), $D_m(S)$ of the solution contained in the second insert (42'), (j) the computation of the difference $$D_{HD} = [D(S) - D(E)] - [D_m(S) - D_m(E)]$$

(k) the computation of the corrected value $V_c(Ver) > V_m(Ver)$ of the bone density of the patient's vertebra (Ver) which meets the equation:

$$V_c(Ver) = V_m(Ver) + \sum_{n=0}^{n} a_n V_c^n(Ver) \cdot D_{HD}$$

the coefficients $a_n$ being those obtained by the operation (g).

The method that has just been described thus makes it possible to correct the measured value $V_m$ of the patient's bone density to obtain the corrected value $V_c$ as a function of the patient's build which is measured by $D_{HD}$.

The method is implemented, when the patient is not there, by means of a phantom simulating the patient including inserts simulating the vertebra and a calibration phantom comprising only two inserts. It is further necessary to use a bag of water to simulate the patient's build. The measurements involved are, therefore, calibration measurements which are done for a given configuration of the scanner so as to define the coefficients a, b and e of the second-degree correction polynomial.

During the bone density measurements made on a patient, all that is needed is the calibration phantom with the two inserts 41' and 42', and not the four or five inserts of the standard method. Furthermore, there is no calibration to be done during the measurements on the patient.

The method has been described chiefly in assuming a correction by means of a second-degree polynomial, but it has been shown that the correction can be done by means of any n degree polynomial. In this case, as indicated above, it is necessary to use (n+1) inserts (39) of different concentrations A0, A1 ... $A_n$, so as to obtain (n+1) equations which make it possible to determine the (n+1) coefficients $a_o$ to $a_n$ of the polynomial:

$$\sum_{n=o}^{n} a_n V_c^n$$

What is claimed is:

1. A method for correcting a measurement of a bone density in an X-ray scanner, comprising the following operations:

(a) positioning, in the field of the scanner, a phantom simulating a body of a patient of slight build and having a cavity formed therein;

(b) positioning, under the simulation phantom, a calibration phantom having two cavities formed therein, in the first of which is disposed a first calibration insert containing water and in the second of which is disposed a second calibration insert containing a solution with a high concentration of di-potassium hydrogen phosphate ($K_2HPO_4$);

(c) positioning, in the cavity of the simulation phantom, an insert which simulates a vertebra and which contains a solution of $K_2HPO_4$ with a concentration A0, and measuring the following densities:

the density $V_c(1)$ of the solution contained in the insert simulating the vertebra;

the density $D_1(E)$ of the water contained in the first calibration insert, and the density $D_1(S)$ of the solution contained in the second calibration insert;

positioning of a bag of water on the simulation phantom, and measuring the following densities:

the density $V_m(1)$ of the solution contained in the insert simulating the vertebra;

the density $D'_1(E)$ of the water contained in the first calibration insert and, the density $D'_1(S)$ of the solution contained in the second calibration insert;

(e) computing $$D_{HD}(1) = [D_1(S) - D_1(E)] - [D'_1(S) - D'_1(E)]$$

which indicates the changing of the density of the solution contained in the second calibration insert due to the presence of the bag of water with respect to the first calibration insert;

(f) reiterating operations (c), (d) and (e), for a number n inserts in addition to the insert containing the solution with the concentration AO, the n inserts containing solutions of $K_2HPO_4$ of concentrations A1 to An from AO and simulating different vertebra, so as to obtain, for each new concentration, other values of $V_c$, $V_m$ and $D_{HD}$.

(g) computing correction coefficients $a_0$ to $a_n$ of an n-degree polynomial such that:

$$V_c = V_m + \sum_{n=0}^{n} a_n V_c^n \cdot D_{HD};$$

(h) measuring the density $V_m(VEL)$ of a patient's vertebra; and (i) correcting the detected density $V_m(VEL)$ using correction coefficients $a_0$ to $a_n$ calculated in the operation (g).

2. A correction method according to claim 1, further comprising the following operation:

(j) computing a mean value of the differences in densities between the $K_2HPO_4$ solution and water for the n inserts simulating the vertebra so as to obtain the difference:

$$\frac{\sum_{i=1}^{n} [D_i(S) - D_i(E)]}{n} = D(S) - D(E)$$

3. A correction method according to claim 2, wherein the operation of measuring the density $V_m(Ver)$ comprises removing the simulation phantom, positioning the patient in the place of the simulation phantom, and measuring the density of a patient's vertebra which is in coincidence with the calibration phantom, and further comprising (1) calculating the following densities while measuring the patient's bone density the density $D_m(E)$ of the water contained in the first calibration insert, and the density $D_m(S)$ of the solution contained in the second calibration insert, and (m) calculating the difference $$D_{HD} = [D(S) - D(E)] - [D_m(S) - D_m(E)];$$

wherein the operation (i) comprises calculating a corrected value $V_c(Ver) > V_m(Ver)$ of the bone density of the patient's vertebra (Ver) which meets the equation:

$$V_c(Ver) = V_m(Ver) + \sum_{n=0}^{n} a_n V_c^n (Ver) \cdot D_{HD}.$$

the coefficients $a_n$ being those obtained by the operation (g).

4. A method of measuring a bone density in an X-ray scanner having a measuring field, comprising the steps of:

(A) placing a simulation phantom in the field of the scanner, and simulation phantom simulating a body of a person having a slight build and having a cavity formed therein;

(B) placing a calibration phantom in the field beneath said simulation phantom, said calibration phantom having first and second cavities formed therein in which are disposed first and second inserts containing first and second reference media;

(C) inserting a solution in said cavity of said simulation phantom, said solution simulating a bone; then (D) measuring densities of said solution and said first and second reference media; then (E) placing a bag of liquid on said simulation phantom; then (F) measuring densities of said solution and said first and second reference media; then (G) calculating the change of density of said second reference medium with respect to said first reference medium due to presence of said bag of liquid; then (H) replacing said solution in said cavity of said simulation phantom with a solution having a different concentration of said chemical;

(I) repeating said steps (D) through (H) a number n times, and then calculating correction coefficients $a_0$ through $a_n$;

(J) measuring the density of a bone; and then (K) correcting the density measured in said step (J) using said correction coefficients calculated in said step (I).

5. A method of measuring a bone density in an X-ray scanner having a measuring field, comprising the steps of:

(A) placing a simulation phantom in the field of the scanner, said simulation phantom simulating a body of a person having a relatively slight build and having a cavity formed therein;

(B) placing a calibration phantom in the field beneath said simulation phantom, said calibration phantom having first and second cavities formed therein in which are disposed first and second inserts containing first and second reference media;

(C) selectively inserting a plurality of solutions in said cavity of said simulation phantom, each having a different solution concentration, and, while each of said plurality of said inserts is present in said cavity of said simulation phantom, performing the following operations (1) measuring the density of the solution then present in said cavity of said simulation phantom and the densities of said first and second reference media, (2) altering said simulation phantom to simulate a body having a relatively heavy build, and (3) measuring, while the simulation phantom is altered to simulate said body having said relatively heavy build, the density of the solution then present in said cavity of said simulation phantom and the densities of said first and second reference media;

(D) calculating, using the densities measured in said step (C), a correction coefficient representative of the effects of differences in body build on measured bone densities;

(E) measuring the density of a bone; and (F) correcting the density measured in said step (E) using said correction coefficient calculated in said step (D).

6. A process according to claim 5, wherein said step of altering said simulation phantom comprises placing a bag of water on said simulation phantom.

7. A process according to claim 5, wherein said step (B) comprises placing said calibration phantom in said field which has said first cavity filled with an insert containing water and said second cavity filled with an insert containing a solution containing a high concentration of $K_2HPO_4$.

8. A process according to claim 7, wherein said step (C) comprises selectively inserting a plurality of inserts each containing a solution having a different concentration of $K_2HPO_4$ in said cavity of said simulation phantom.

9. A process according to claim 8, wherein said step (E) comprises measuring the density of a vertebra.

10. A process according to claim 5, wherein said step (F) comprises correcting said measured density according to a second degree polynomial.

* * * * *